United States Patent [19]
Masayuki et al.

[11] Patent Number: 5,985,811
[45] Date of Patent: Nov. 16, 1999

[54] CLEANING SOLUTION AND CLEANING METHOD

[75] Inventors: Toda Masayuki, Yamagata-ken; Tadahiro Ohmi, Miyagi-ken; Yasuyuki Harada, Juchu, all of Japan

[73] Assignees: Tadhiro Ohmi, Miyagi-ken; Pre-Tech Co., Ltd.; Kabushiki Kaisha Ultraclean Technology Research Institute, both of Tokyo, all of Japan

[21] Appl. No.: 08/780,502

[22] Filed: Jan. 8, 1997

[30]     Foreign Application Priority Data

Jan. 17, 1996 [JP] Japan ................................. 8-005400

[51] Int. Cl.$^6$ ................................. B08B 3/04; B08B 3/12
[52] U.S. Cl. ........................ 510/175; 510/370; 510/405; 134/1.3
[58] Field of Search .................................. 510/175, 370, 510/405; 134/1.3

[56] References Cited

U.S. PATENT DOCUMENTS

| | | | |
|---|---|---|---|
| 4,820,473 | 4/1989 | Ohashi et al. ........................... | 376/305 |
| 5,180,403 | 1/1993 | Kogure ...................................... | 55/53 |
| 5,422,013 | 6/1995 | Hirofuji .................................... | 210/739 |
| 5,571,419 | 11/1996 | Obata et al. ............................. | 210/664 |
| 5,589,005 | 12/1996 | Ohmi ......................................... | 134/30 |
| 5,698,040 | 12/1997 | Guldi et al. ............................. | 134/1.3 |
| 5,888,357 | 3/1999 | Mitsumori et al. ...................... | 134/1.3 |

*Primary Examiner*—Jerry D. Johnson
*Attorney, Agent, or Firm*—Randall J. Knuth

[57]  ABSTRACT

A cleaning solution and cleaning method are provided which: (1) make treatment at room temperature possible, and do not require heating, (2) use little chemicals and water, (3) do not require specialized apparatuses, and moreover, (4) do not require the use of specialized chemicals. The cleaning solution of the present invention comprises pure water containing 20 ppb–100 ppb of oxygen and 2 ppb or more of nitrogen. Furthermore, the cleaning solution may comprise electrolytically ionized water containing OH$^-$ and containing 20 ppb–100 ppb of oxygen. In the cleaning method of the present invention, the cleaning of a material to be cleaned is conducted in a cleaning solution comprising pure water containing 20 ppb–100 ppb of oxygen and 2 ppb–15 ppm of nitrogen, while applying ultrasound having a frequency of 30 kHz or more. Furthermore, in the cleaning method of the present invention, the cleaning of a material to be cleaned may be conducted in a cleaning solution comprising electrolytically ionized water containing OH$^-$ and containing 20 ppb–100 ppb of oxygen, while applying ultrasound having a frequency of 30 kHz or more.

53 Claims, 10 Drawing Sheets

Fig. 3
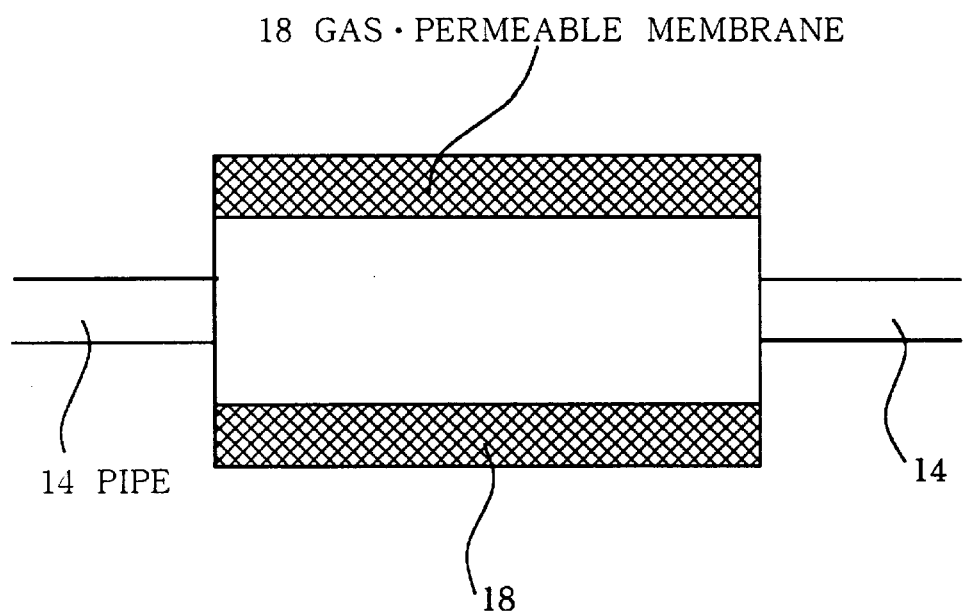
(a)
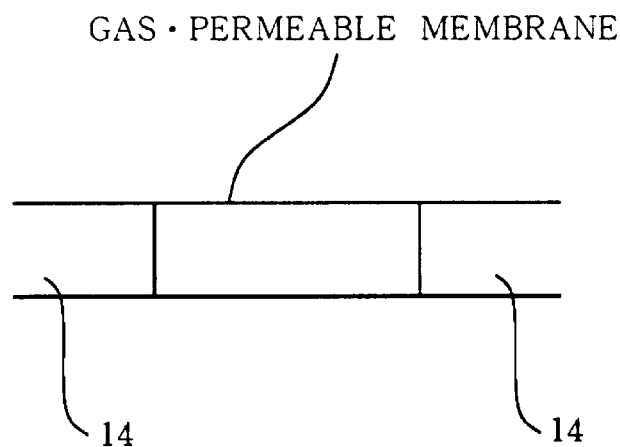
(b)

Fig. 6

○ $NH_4^+$ formation reactions $$H_2O \rightarrow \cdot OH + \cdot H$$

$$N_2 + 6 \cdot H \rightarrow 2NH_3$$

$$NH_3 + H_2O \rightarrow \cdot NH_4^+ + OH^-$$

○ $NH_2^-$ formation reactions $H_2O \rightarrow \cdot OH + \cdot H$     $N_2 + 4 [O] + 2 \cdot H \rightarrow 2NO_2^- + 2H^+$ $\cdot OH + \cdot OH \rightarrow H_2O_2$     $NH_3 + 3 \cdot OH + 2 [O] + \cdot H \rightarrow NO_2^- + H^+ + 3H_2O$ $H_2O_2 \rightarrow H_2O + [O]$ ○ $NH_3^-$ formation reactions $H_2O \rightarrow \cdot OH + \cdot H$     $N_2 + 6 [O] + 2 \cdot H \rightarrow 2NO_3^- + 2H^+$ $\cdot OH + \cdot OH \rightarrow H_2O_2$     $NH_3 + 3 \cdot OH + 3 [O] + \cdot H \rightarrow NO_3^- + 3H_2O + H^+$ $H_2O_2 \rightarrow H_2O + [O]$     $NO_2^- + [O] \rightarrow NO_3^-$ REACTIONS OCCURRING WHEN ULTRASOUND
IS APPLIED TO PURE WATER CONTAINING Ar AND $N_2$

CLEANING SOLUTION AND CLEANING METHOD

TECHNOLOGICAL FIELD

The present invention relates to a cleaning solution and cleaning method, and in greater detail, relates to a cleaning solution and cleaning method which are capable of ultra-pure cleaning using a greatly reduced number of processes in comparison to conventional methods, and without conducting heating.

BACKGROUND TECHNOLOGY

Recently, the semiconductor devices which are formed on the surface of semiconductor substrates have become highly dense and minute, reaching the sub-micron level. In order to achieve this high density, it is necessary to maintain the surface of the substrate in an ultra-clean state. That is to say, it is necessary to remove organic material, metals, various types of particles, and oxides (oxide films) from the surface of the substrate. It is for this reason that the surface of the substrate is cleaned.

Conventionally, a cleaning method comprising the following processes was known as cleaning technology for achieving an ultra-clean substrate surface.

(1) 98% $H_2SO_4$/ 30% $H_2O_2$ (component ratio 4:1); temperature 130° C.

By means of this process, organic matter and metals were removed.

(2) ultra-pure water cleaning; room temperature (3) dilute HF cleaning; room temperature By means of this process, oxide films were removed.

(4) ultra-pure water cleaning; room temperature (5) 28% $NH_4OH$/ 30% $H_2O_2$/ $H_2O_2$ (component ratio 1:1:5); temperature 80–90° C.

By means of this process, particles were removed.

(6) ultra-pure water cleaning; room temperature (7) dilute HF cleaning; room temperature In process (5) above, $H_2O_2$ was employed, so that oxide films were formed in this process (5); in process (7), these oxide films were removed.

(8) ultra-pure water cleaning; room temperature (9) 36% HCl/ 30% $H_2O_2$/ $H_2O$ (component ratio 1:1:6); temperature 80–90° C.

In this process, metals were removed.

(10) ultra-pure water cleaning; room temperature

(11) dilute HF cleaning; room temperature

In process (9) above, $H_2O_2$ was employed, so that an oxide film was formed in this process (9); in process (11), this oxide film was removed.

(12) ultra-pure water cleaning; room temperature

However, in the conventional cleaning method described above, a variety of problems were present.

The number of processes was very large, comprising 12 in total.

The amount of chemicals and water employed was large.

The method encompassed high temperature processes. Accordingly, the vapor pressures of the chemical solutions were also high, and the clean room environment inevitably became contaminated.

Both acidic and alkaline chemicals were employed, so that the recovery of the chemicals was difficult. Furthermore, the waste liquid treatment was high in cost.

In semiconductor devices, metal wiring comprising aluminum or the like is formed on the substrate; however, when such metallic wiring is exposed, the metallic wiring may be dissolved in the chemical solutions in an undesirable manner, so that in such cases, such chemical solutions can not be employed.

In order to solve these problems, the following technology was developed. This cleaning method (Japanese Patent Application No. Hei 7-108840), encompassed the following processes: a first process in which cleaning was conducted using pure water containing ozone; a second process, in which cleaning was conducted by means of a cleaning solution containing HF, $H_2O_2$ and/or $O_3$, water, and a surfactant, while applying vibration at a frequency of 500 kHz or more; a third process in which cleaning was conducted using pure water; and a fourth process in which oxide films were removed.

The following effects were achieved by means of this technology.

① The number of processes was greatly reduced.

② Treatment was possible at room temperature; heating was not required.

③ The amount of chemicals and water employed was reduced.

④ Only acidic chemicals were employed, so that their recovery was a simple matter.

Moreover, in the second process of this technique, HF was employed and ultrasonic vibration applied in order to remove particles. For this reason, the vessel described below was developed for use as the cleaning vessel. This cleaning vessel (Japanese Patent Application No. Hei 7-108840) comprised metal, had a nickel fluoride layer formed on at least the inner surfaces of the cleaning solution storage tank, and had a further carbon layer formed on the nickel fluoride layer; a vibrator was attached to the outer surface of the vessel.

That is to say, the cleaning method disclosed in Japanese Patent Application No. Hei7-108840 was highly advantageous; however, the use of the specialized cleaning vessel described above was necessary.

Furthermore, in the second process, strongly oxidizing components ($H_2O_2$, $O_3$) were contained at high concentrations. For example, hydrogen peroxide ($H_2O_2$) was contained in an amount within a range of 0.1–20 weight %, while ozone ($O_3$) was contained at a level of 2 ppm or more. For this reason, it was necessary to employ apparatuses which were resistant to corrosion by means of these components.

The present invention has as an object thereof to provide a cleaning solution and a cleaning method which: ① are capable of treatment at room temperature, without the necessity of heating; ② reduce the amount of chemicals and water employed; ③ do not require the use of specialized apparatuses; and moreover ④ do not require the use of specialized chemicals.

(Disclosure of the Invention)

The cleaning solution of the present invention, which solves the problems described above, contains, in pure water, 20 ppb –100 ppb of oxygen, and 2 ppb or more of nitrogen.

Furthermore, the cleaning solution contains, in electrolytically ionized water containing $OH^-$, 20 ppb–100 ppb of oxygen.

In the cleaning method in accordance with the present invention, a material to be cleaned is cleaned in a cleaning solution in which 20 ppb–100 ppb of oxygen and 2 ppb–15 ppm of nitrogen are contained in pure water, while applying vibration of 30 kHz or more.

Furthermore, in the cleaning method, the cleaning of a material to be cleaned is conducted in a cleaning solution in which 20 ppb–100 ppb of oxygen are contained in electrolytically ionized water containing OH⁻, while applying vibration of 30 kHz or more.

(Function)

In the present invention, a cleaning solution is employed which contains 20 ppb–100 ppb of oxygen and 2 ppb or more of nitrogen. During cleaning, vibration having a frequency of 30 kHz or more is applied.

By means of this, the percentage of particles such as silica, alumina, or the like which is removed can be dramatically increased.

This is thought to be due to the following mechanism.

When vibration is applied to pure water containing oxygen and nitrogen, OH (OH radical), H (hydrogen radical), and O (atomic oxygen) radicals are generated in accordance with the following formulas.

$$H_2O \rightarrow \cdot H + \cdot OH \quad \text{Formula 1}$$

$$O_2 \rightarrow 2O \quad \text{Formula 2}$$

$$O + \cdot H \rightarrow \cdot OH \quad \text{Formula 3}$$

The reaction shown in Formula 1 above may occur in an environment in which 2 ppb or more nitrogen gas is present. The theoretical basis for this is unclear; however, it has been experimentally verified. FIG. 5 shows a graph indicating the relationship between the amount of nitrogen contained and the amount of OH (OH radicals) generated, which was determined by means of experimentation; it can be seen that OH (OH radicals) is generated in pure water containing nitrogen in an amount of 2 ppb or more.

In the presence of these radicals, the following reactions take place.

$$\cdot OH + \cdot OH \rightarrow H_2O_2 \quad \text{Formula 4}$$

$$\cdot H + \cdot H \rightarrow H_2 \quad \text{Formula 5}$$

$$H_2O_2 \rightarrow \cdot O + H_2O \quad \text{Formula 6}$$

$$N_2 + 6 \cdot H \rightarrow 2NH_3 \quad \text{Formula 7}$$

$$NH_3 + H_2O \rightarrow NH_4^+ + OH^- \quad \text{Formula 8}$$

Formulas 6, 7, and 8 above are grouped together and shown in FIG. 6. When the reactions shown in FIGS. 1 through 8 above take place, $NO_2^-$ and $NO_3^-$ are generated. In order to facilitate understanding of these reactions, they are shown together in FIG. 6. Furthermore, the relationships among Formulas 1 through 8 are shown in FIG. 7.

Atomic O and OH (OH radicals) react with the organic material on the surface of the substrate, and this organic material is removed from the surface. When the organic material is removed, the surfaces of the substrate which were isolated by the organic material are exposed.

In the presence of atomic oxygen (O), the $NH_3$, which is generated as a result of the reaction of hydrogen radicals (H) with dissolved $N_2$, reacts with $H_2O$, and the resulting OH⁻, or the OH⁻ generated by the electrolysis of the water, tends to oxidize the exposed surfaces.

That is to say, the Si is etched as a result of the following reactions:

| Si + O + 2OH⁻ |
|---|
| → H₂SiO₃ |
| → 2H+ + SiO₃ |

In addition to the etching of the Si surface, the particles which are deposited thereon are lifted away from the surface and removed. In the final analysis, the particles are not removed by means of a direct reaction, but by means of the etching of the Si beneath the particles.

This is shown in FIG. 8. FIG. 8 shows the mechanism of the removal of the particles from the Si surface when an oxide film is not formed on that surface. However, when an oxide film ($SiO_2$) is formed on the surface, the particles are removed by the dissolution of the $SiO_2$ by means of OH⁻. This is shown in FIG. 9.

As described above, the presence of 2 ppb or more of nitrogen is considered to be essential both from the point of view of the generation of OH⁻ and the generation of $NH_3$.

When electrolytically ionized water is employed, OH⁻ is already present, so that nitrogen need not be contained. However, nitrogen may also be present.

(Embodied Modes of the Invention)

Hereinbelow, embodied modes of the present invention will be analyzed by structural requirements.

(Oxygen)

In the present invention, oxygen is contained in pure water or in electrolytically ionized water.

The amount contained is an important characteristic, and is within a range of 20 ppb–100 ppb; only within this range is the percentage of particles removed extremely high.

As shown in FIG. 4, at amounts of less than 20 ppb, particles can not be removed. Accordingly, it is necessary to have 20 ppb or more.

On the other hand, when oxygen is present in excess of 100 ppb, the percentage of particles removed begins to worsen precipitously. The reason for this is unclear; however, at levels of more than 100 ppb, oxide film formation is increased, and this is thought to bring about a decline in the percentage of particles removed.

In the present invention, the amount of oxygen contained is set at 100 ppb or less.

A range of 50 ppb–100 ppb shows particularly superior particle removal, so that such a range is preferable.

(Nitrogen)

As described above, the presence of 2 ppb or more of nitrogen is necessary in order to generate OH⁻ and $NH_3$. The amount of OH⁻ generated essentially corresponds to the percentage of particles removed (FIG. 5).

(Ultrasound)

In the present invention, ultrasound having a frequency of 30 kHz or more is applied to the cleaning solution. By means of applying this ultrasound, it is possible to generate different kinds of radicals. Accordingly, the frequency of the ultrasound which is applied should be set to the frequency which is necessary to generate radicals. This frequency varies based on the amount of oxygen and nitrogen contained; however, a frequency of 30 kHz or higher is necessary.

In particular, a frequency within a range of 500 kHz–3 MHz is preferable. When the frequency is 500 kHz or higher, in addition to the generation of radicals, it is also possible to remove products generated by the etching of the substrate surface from the surface, and the efficiency of particle removal is further increased.

(Pure Water, Electrolytically Ionized Water)

The pure water employed in the present invention encompasses a variety of grades; the following type is preferable.

Resistivity: 18.0 MΩ
Metal concentration: 1 ppt or less
Impurity concentration: 10 ppb or less Such a grade of water is termed ultra-pure water.

Furthermore, the electrolytically ionized water is water which contains $H^+$ ions or $OH^-$ ions generated by means of the electrolysis of water; that described in Japanese Patent Application, First Publication No. Hei 6-260480, for example, may be employed. In the present invention, water containing $OH^-$ ions is employed.

(Impurities)

It is particularly preferable that the impurities present in the cleaning solution be at a level of 10 ppb or less. What is meant by impurities here are gases other than oxygen and nitrogen, ions other than those appearing in Formulas 1 through 8, organic materials, inorganic materials and metallic ions.

When the impurities are so controlled as to be at a level of 10 ppb or less, the effectiveness of particle removal is dramatically improved. The reason for this unclear; however, it is thought that the impurities react with the radicals and ions shown in Formulas 1 through 8, and that the number of radicals or ions contributing to particle removal is thus reduced.

During storage of the cleaning solution, if the cleaning solution comes into contact with air, impurities will enter, since even the air within a clean room contains components other than oxygen and nitrogen (for example, carbon dioxide, and various ions); it is thus necessary to store the cleaning solution so as not to come into contact with the atmosphere.

Furthermore, it is preferable that the cleaning solution not come into contact with the air during cleaning, in order to prevent the admixture of impurities into the solution, and for this reason, a cleaning method in which the cleaning solution is sprayed onto the material to be cleaned is preferable. Furthermore, in order to avoid contact between the air and the cleaning solution during cleaning, it is preferable that a gas curtain comprising an inert gas be provided above the cleaning solution within the vessel. When a gas curtain is provided, the inert gas dissolves in the cleaning solution, and it is possible to generate a large number of H radicals, OH radicals, or other ions.

(Cleaning Apparatus)

A cleaning apparatus is employed which uses immersion cleaning; such an apparatus is shown in FIG. 1.

In the Figure, reference 1 indicates the cleaning vessel; cleaning solution 3 is stored within this vessel. A vibrator 2 is provided on the bottom surface of cleaning vessel 1 in order to apply ultrasound to cleaning solution 3. Reference 6 indicates a gas introduction pipe; this serves to supply oxygen, nitrogen, argon, or a mixed gas of one or more of these gases to cleaning solution 3. Reference 5 indicates a sensor, which detects the composition of cleaning solution 3. The signals from sensor 5 are sent to a control apparatus (not depicted in the figure), and the amount of gas supplied to gas introduction pipe 6 is thereby controlled.

Reference 4 indicates a gas curtain. This gas curtain 4 prevents contact between cleaning solution 3 and the atmosphere, and serves to prevent changes in the composition of cleaning solution 3 resulting from contact with the atmosphere (changes in the oxygen concentration, changes in the nitrogen concentration, entry of impurity gases, ions, organic material, or the like). This gas curtain 4 is formed by causing an inert gas to flow from gas supply element 7 in such a fashion as to be parallel to the surface of the cleaning solution 3. The gas which flows from gas supply element 7 is collected by a gas collecting element which is positioned in opposition to the gas supply element, and the gas is then conveyed to the exterior as exhaust. It is preferable that an ultrapure gas having an impurity concentration of a few ppt or less be employed as the inert gas. Argon gas is preferable. It is also possible to employ nitrogen gas.

The material to be cleaned is moved down through the gas curtain 4 and immersed into cleaning solution 4.

(Cleaning Apparatus 2)

The apparatus which is shown in FIG. 2 employs spray cleaning.

In FIG. 2, reference 1 indicates the cleaning vessel. The material to be cleaned 9 is supported on a rotating support element 10, and this material to be cleaned 10 is rotated during cleaning.

The cleaning solution 13 is stored in tank 15. This cleaning solution may be adjusted in advance to predetermined concentrations. The cleaning solution 13 is sprayed onto the material to be cleaned 9 by means of nozzle 11 and via pipe 14. An ultrasonic vibrator is provided in the vicinity of the opening of nozzle 11, and ultrasound is applied to the cleaning solution which passes through nozzle 11. By means of applying ultrasound, highly reactive H (H radicals) and OH (OH radicals) are generated in the pure water.

In this structure, the tank 15, pipe 14 and nozzle 11 should all be isolated from the atmosphere, and should comprise metal.

If the concentrations are adjusted in advance, when the cleaning solution is stored in tank 15 over a long period of time, changes will occur in the concentrations; it is thus preferable that the oxygen and nitrogen be placed in the pure water when it is to be used. In order to accomplish this, as shown in FIG. 3, a cylinder (FIG. 3(a)) comprising a gas (oxygen or nitrogen) permeable membrane or pipe comprising such a membrane (FIG. 3(b)), is provided in pipe 14, and by means of appropriately designing the permeability of this permeable membrane, it is possible to cause oxygen or nitrogen to be contained within the pure water as it is supplied from tank 15 to nozzle 11. A membrane comprising Teflon (a registered trademark) may be used as the permeable membrane.

(Cleaning Apparatus 3)

In FIG. 10, another example of a cleaning apparatus is shown. This example is a cleaning apparatus which conducts rear surface cleaning.

In FIG. 10, reference 9 indicates a semiconductor substrate (wafer) or the like which is the material to be cleaned. Reference 19 indicates a support element for supporting wafer 9. This support element supports wafer 9 at the periphery thereof, and the central portion thereof is hollow.

The cleaning solution is sprayed from nozzle 20 in an upwards direction. A vibrator 21 for applying ultrasound to the cleaning solution is provided in the vicinity of the opening of nozzle 20. Support element 19 can be rotated.

Furthermore, although this is not shown in the figure, a nozzle such as that shown in FIG. 2 may be provided above wafer 9. By means of this, it is possible to simultaneously conduct the cleaning of the upper and lower surfaces of wafer 9.

(Another Cleaning Apparatus)

In FIG. 11, another cleaning apparatus is shown.

In FIG. 11, reference 29 indicates a semiconductor wafer which is the material to be cleaned. Reference 30 indicates a support element which supports the material to be cleaned 29. This support element 30 may be rotated. Reference 31 indicates a nozzle. An ultrasonic vibrator 32 for applying ultrasound to the cleaning solution is provided in the vicinity of the opening of nozzle 31.

In the present example, the cleaning solution is emitted from nozzle 31 in the form of a mist. The cleaning solution mist falls onto the upper surface of semiconductor 29. The cleaning solution mist remains on the semiconductor wafer 29 in a mist state, and conducts the removal of particles. With the passage of time, the cleaning solution mist forms droplets and is removed from the surface of wafer 29 by centrifugal force together with the particles which are removed.

When such an apparatus is employed, the amount of cleaning solution employed can be reduced.

(Medical Supplies, Foodstuffs)

The cleaning solution may also be employed in the cleaning of medical supplies (medicines), and foodstuffs. In such cases, the disinfection effects are particularly superior.

(Surfactant)

In the present invention, a surfactant may be added to the cleaning solution. When a surfactant is added, the surface roughness may be reduced, or variations in the surface roughness may be reduced.

Examples of surfactants which may be used include anionic types, cationic types and nonionic types. Furthermore, hydrocarbon types or fluorocarbon types may be employed. Non-ionic surfactants which have the effect of lowering the surface tension of the solution are particularly preferable.

There are cases in which the surfactant cannot be removed by rinsing, depending on the type of surfactant employed. In such cases, cleaning may be conducted by applying ultrasound to ozonated ($O_3$) ultrapure water.

BRIEF DESCRIPTION OF THE DRAWINGS

FIG. 3 is a schematic diagram showing a method for the introduction of oxygen or nitrogen.

FIG. 6 shows the formula describing reactions occuring during the application of ultrasound to ultrapure water containing inert gases (for example, Ar gas or $N_2$ gas).

DESCRIPTION OF THE REFERENCES 1 cleaning vessel,
2 ultrasonic vibrator,
3 cleaning solution,
4 inert gas gas curtain,
5 concentration sensor,
6 gas (oxygen, nitrogen) introduction pipe,
7 gas supply element,
8 gas collecting element,
9 material to be cleaned (semiconductor wafer),
10 rotating support element,
11 nozzle,
12 ultrasonic vibrator,
13 cleaning solution (pure water, electrolytically ionized water),
14 pipe,
15 tank,
18 gas permeable membrane,
19 material to be cleaned (semiconductor wafer),
20 nozzle,
21 ultrasonic vibrator,
29 material to be cleaned (semiconductor wafer),
30 support element,
31 nozzle,
32 ultrasonic vibrator,
33 cleaning solution in mist form.

(Best Mode for Carrying Out the Present Invention)

Hereinbelow, embodiments of the present invention will be explained. It is of course the case that the present invention is in no way limited to the embodiments described below.

Figure 1:
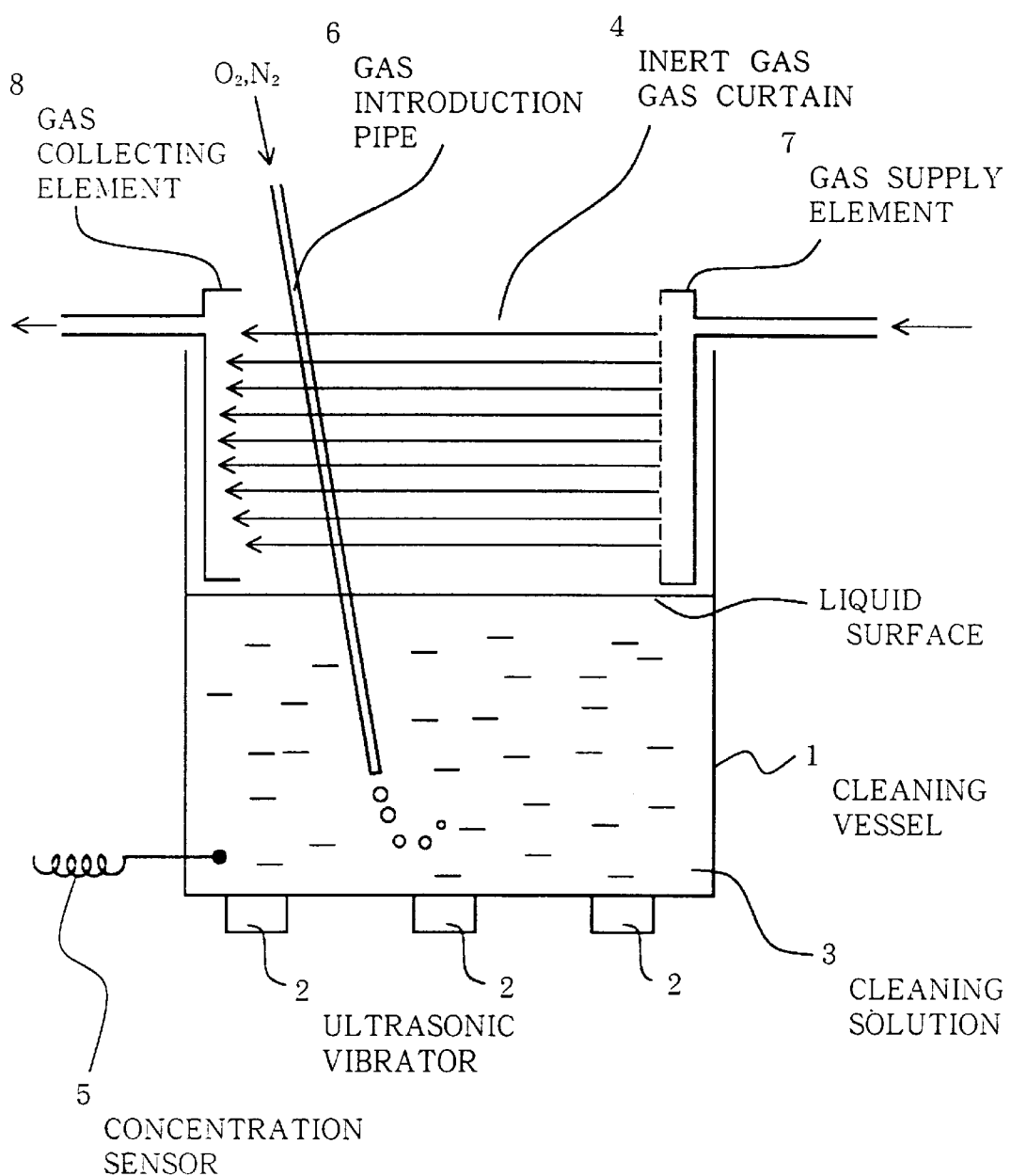
FIG. 1 is a schematic diagram showing an immersion type cleaning apparatus.

In the present embodiment, cleaning was conducted using the cleaning apparatus shown in FIG. 1.

That is to say, after storing pure water in vessel 1, an air curtain was formed by causing a flow of argon gas having an impurity concentration of 5 ppb or less from gas supply element 7, and cleaning solution 3 was thus isolated from the atmosphere.

Oxygen and nitrogen were supplied in that order to cleaning solution 3 from gas introduction pipe 6 by means of bubbling, and the oxygen and nitrogen concentrations, and surfactant concentration, in the cleaning solution were set to the predetermined values given below.

As the ultra-pure water, a silicon wafer (4 inches in diameter) having a surface (100) was employed as the material to be cleaned.

Polystyrene latex (PSL) granules having an average particle diameter of 0.22 μm were deposited on this silicon wafer, and then this silicon wafer was moved down through air curtain 4 and immersed in cleaning solution 3, and ultrasonic cleaning was conducted under the following conditions.

Ultrapure Water:

Resistivity 18.0 MΩ

Metallic Concentration 1 ppt or less

Impurity Concentration 10 ppb or less

Oxygen Concentration: 60 ppb

Nitrogen Concentration: 10 ppm

Surfactant: non-ionic surfactant

Ultrasound: 600 kHz

Cleaning Period: 10 minutes

Cleaning Solution Temperature: room temperature

After the cleaning described above, the number of adhering particles was determined using a particle counter. The results are as shown in Table 1, broken down by particle diameter; superior removal effectiveness was achieved at all particle diameters.

TABLE 1

| Particle Diameter | Before cleaning | After cleaning | Removal Efficiency |
| --- | --- | --- | --- |
| 0.3–0.5 µm | $3.5 \times 10^3$ | $4.4 \times 10^2$ | 96% |
| 0.5–1 µm | $3.4 \times 10^3$ | $1.0 \times 10^2$ | 97% |
| 1 µm or more | $3 \times 10^3$ | $3 \times 10^2$ | 99% |

As shown in Table 1, the present embodiment exhibits superior particle removal effects.

(Embodiment 2)

In the present embodiment, the effects of oxygen concentration were investigated. The oxygen concentration was varied as in embodiment 1.

Measurement of removal efficiency was conducted in the same manner as in embodiment 1.

Figure 4:
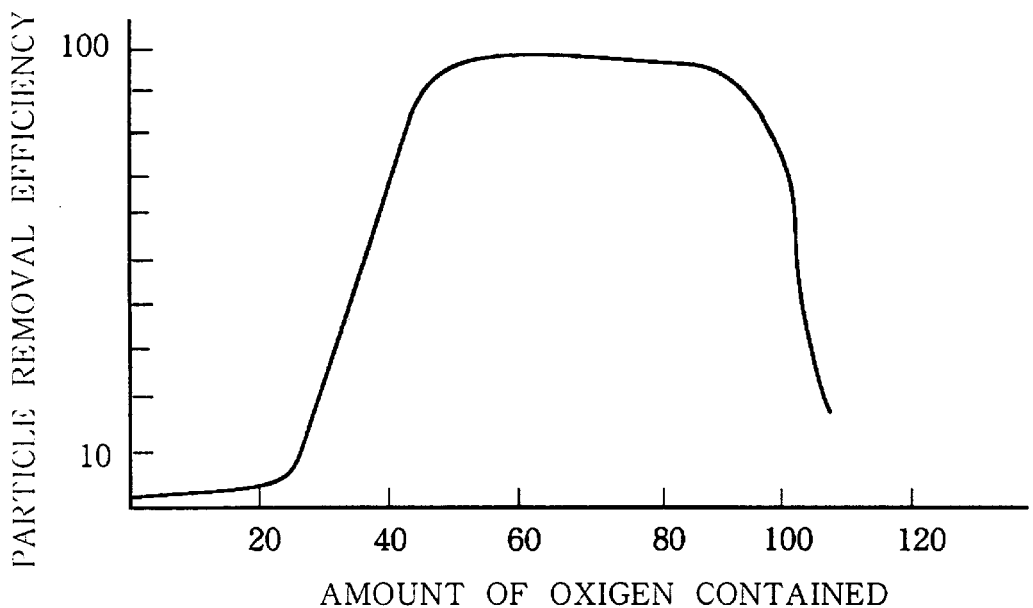
FIG. 4 is a graph showing the experimentally obtained relationships between the amount of oxygen contained and the effectiveness of particle removal.

The results thereof are shown in FIG. 4. The removal efficiency which is shown in FIG. 4 refers to the removal of particles having a size within a range of 0.3–0.5 µm.

As is clear from FIG. 4, removal effects begin to be generated at an amount of oxygen contained of 20 ppb. In particular, the removal effect increases dramatically beginning at 50 ppb. That is to say, it was learned that a range of 50 ppb–100 ppb is preferable in terms of the efficiency of particle removal.

(Embodiment 3)

In the present embodiment, the effects of nitrogen concentration were investigated. That is to say, everything was conducted as in embodiment 1 with the exception of nitrogen concentration, and the nitrogen concentration was varied.

The efficiency of removal was measured in the same manner as in embodiment 1.

Figure 5:
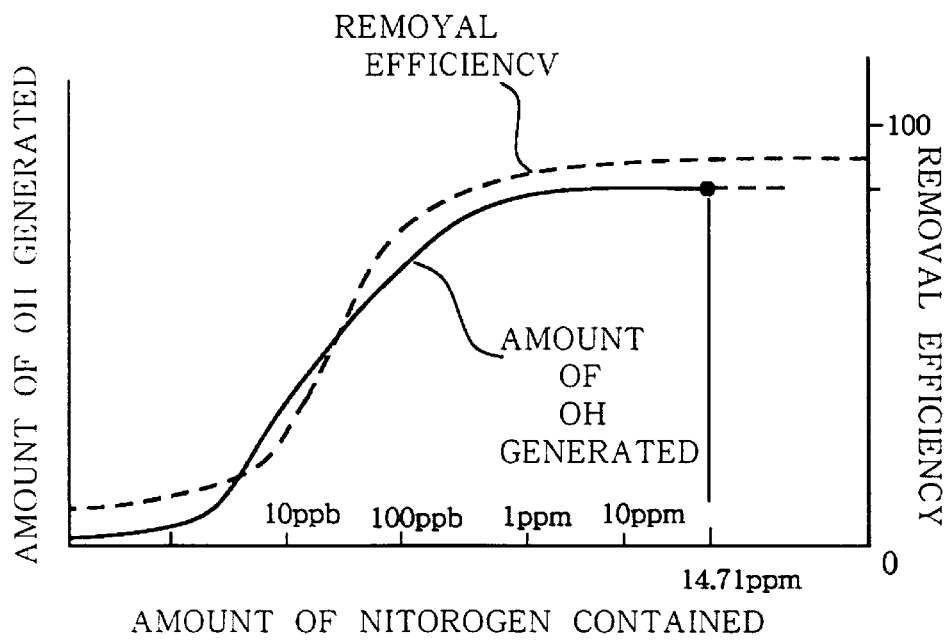
FIG. 5 is a graph showing the experimentally obtained relationship between the amount of nitrogen contained and the effectiveness of particle removal and the amount of OH⁻ generated.
Figure 7:
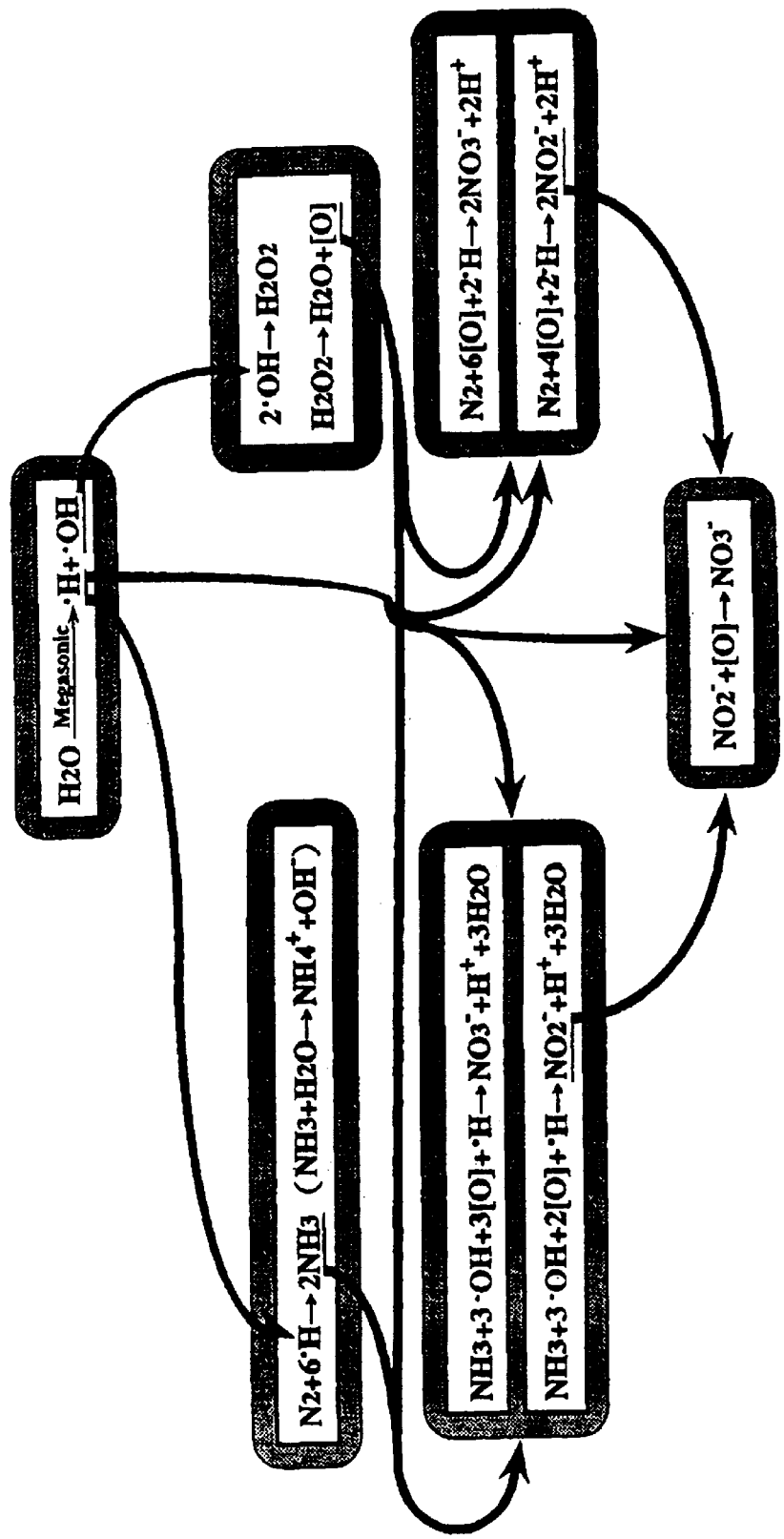
FIG. 7 shows the relationship between the various formulas describing reactions occurring when ultrasound is applied to ultrapure water containing inert gas (for example, Ar gas or $N_2$ gas).
Figure 8:
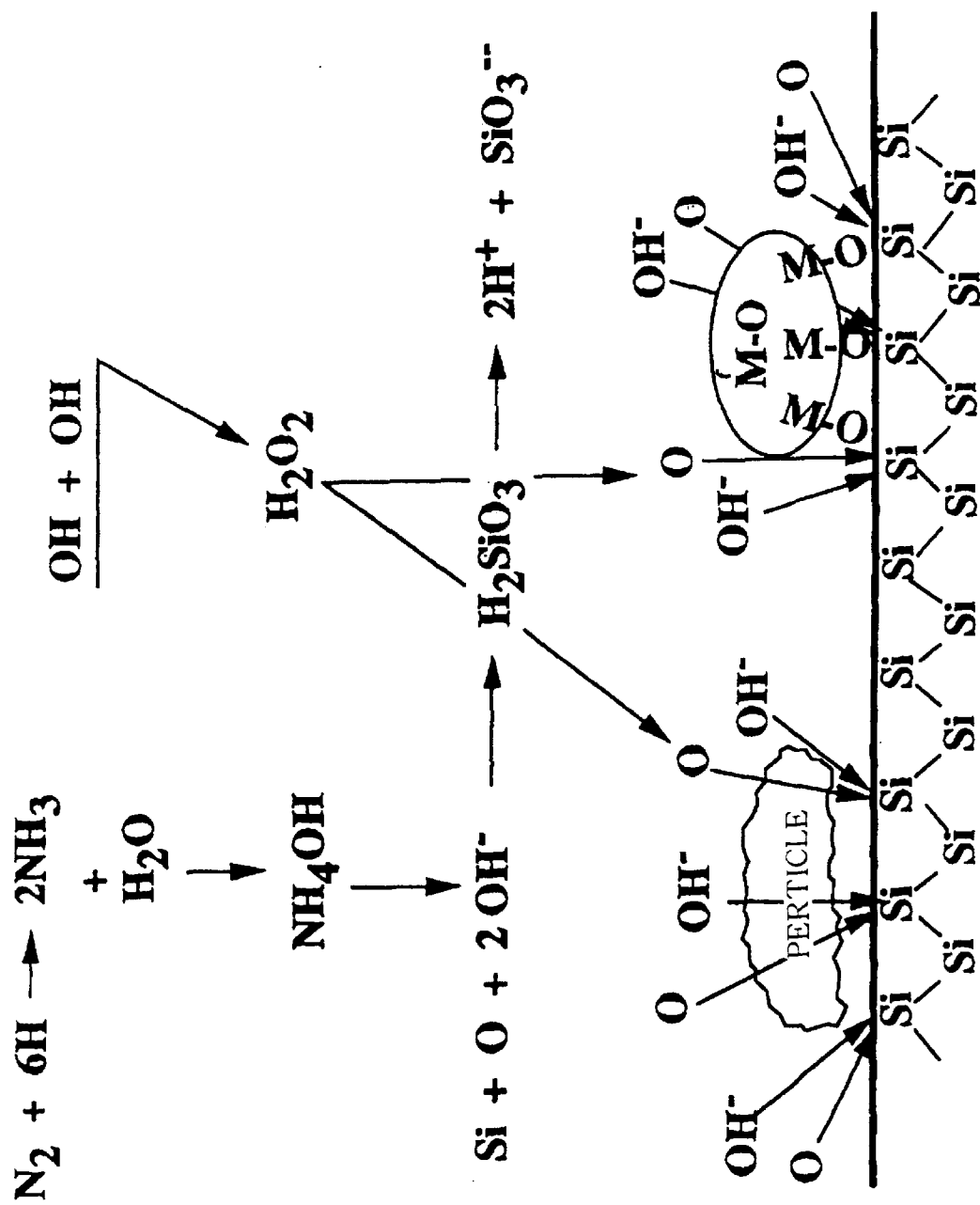
FIG. 8 is a schematic diagram showing a mechanism for the removal of particles from a Si surface.
Figure 9:
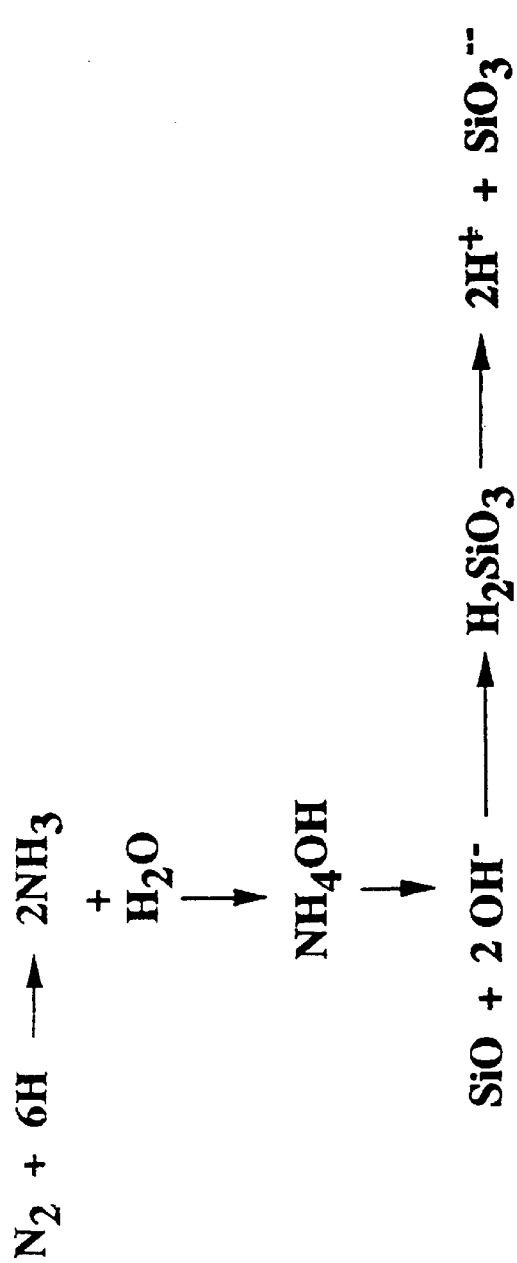
FIG. 9 is a schematic diagram showing a mechanism for the removal of particles from a $SiO_2$ surface.
Figure 10:
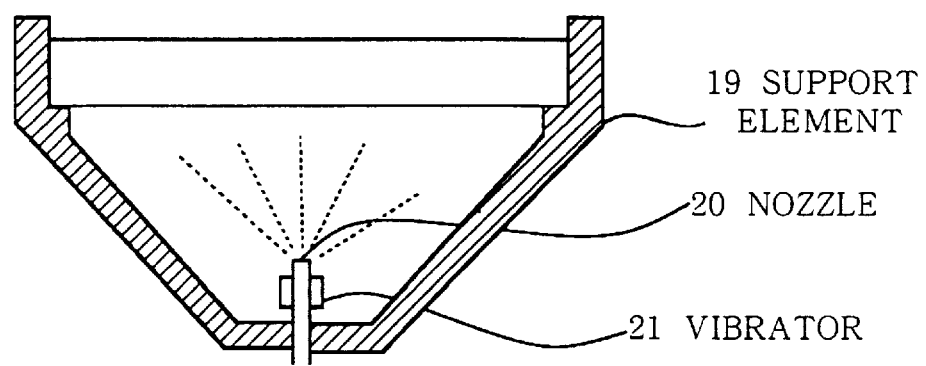
FIG. 10 is a schematic diagram showing a cleaning apparatus.
Figure 11:
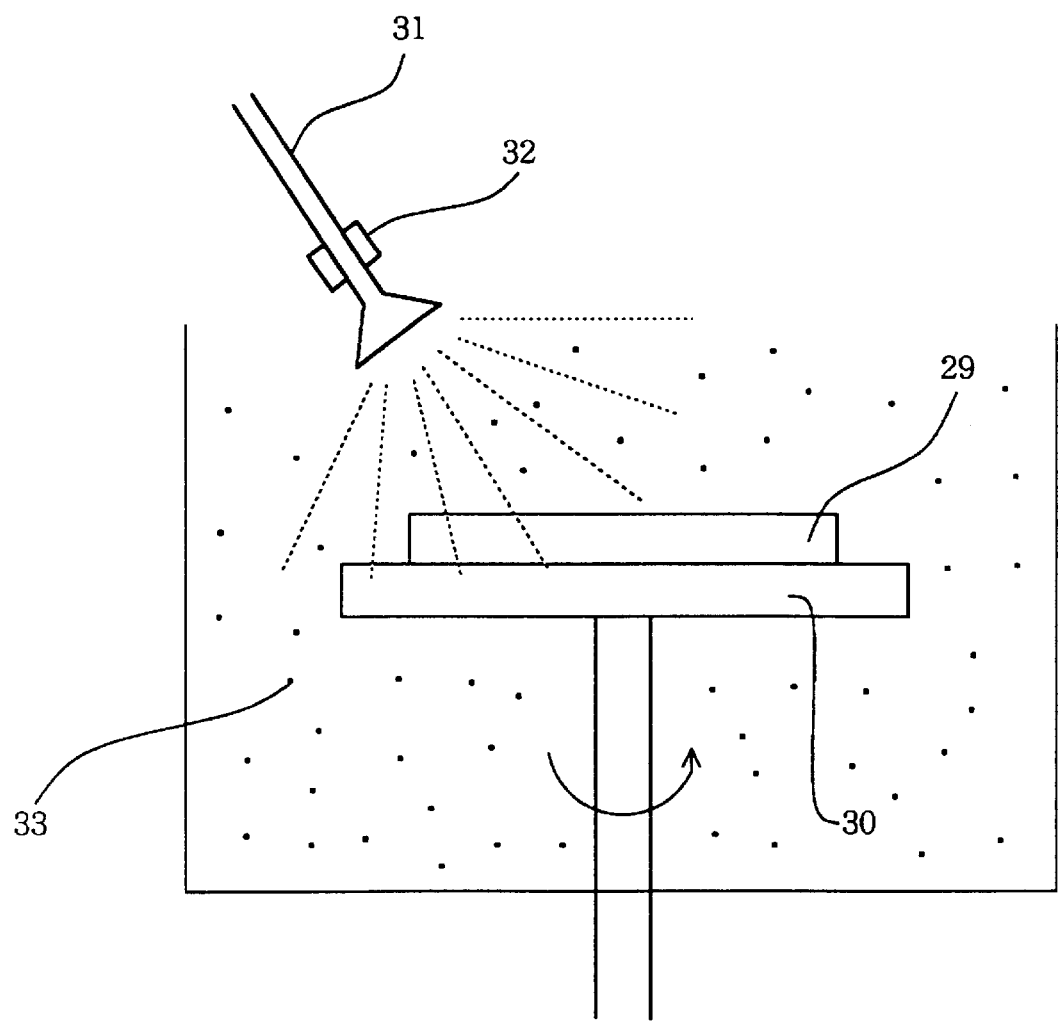
FIG. 11 is a schematic diagram showing another cleaning apparatus.

The results thereof are shown in FIG. 5. The removal efficiency shown in FIG. 5 refers to the removal of particles having a size within a range of 0.3–0.5 µm.

At amounts of nitrogen contained of 100 ppb or more, the effect of particle removal is saturated. Furthermore, the saturation amount of nitrogen is approximately 15 ppm (at standard temperature and pressure), and identical removal efficiencies were attained at this saturation amount.

(Embodiment 4)

In the present embodiment, the effects of the ultrasonic frequency were investigated.

The removal efficiencies were as given below.

The present embodiment was identical to embodiment 1 with the exception of the frequency, and the removal efficiency refers to particles having a size within 0.3–0.5 µm.

| 30 KHz | 92% |
| 100 KHz | 93% |
| 600 KHZ | 96% |
| 1 MHZ | 97% |
| 3 MHz | 97% |

At frequencies of 600 kHz or more, the removal efficiency was higher than that at lower frequencies However, the removal efficiency was saturated at 600 kHz or more.

(Embodiment 6)

In the present embodiment, electrolytically ionized water was employed in place of ultrapure water. This embodiment was identical to embodiment 1 in all other respects.

A slightly higher removal efficiency was observed using electrolytically ionized water (containing OH⁻ ions) than that in embodiment 1. This is thought to be connected to the fact that the electrolytically ionized water itself contains OH⁻ ions from the beginning.

(Embodiment 7)

Figure 2:
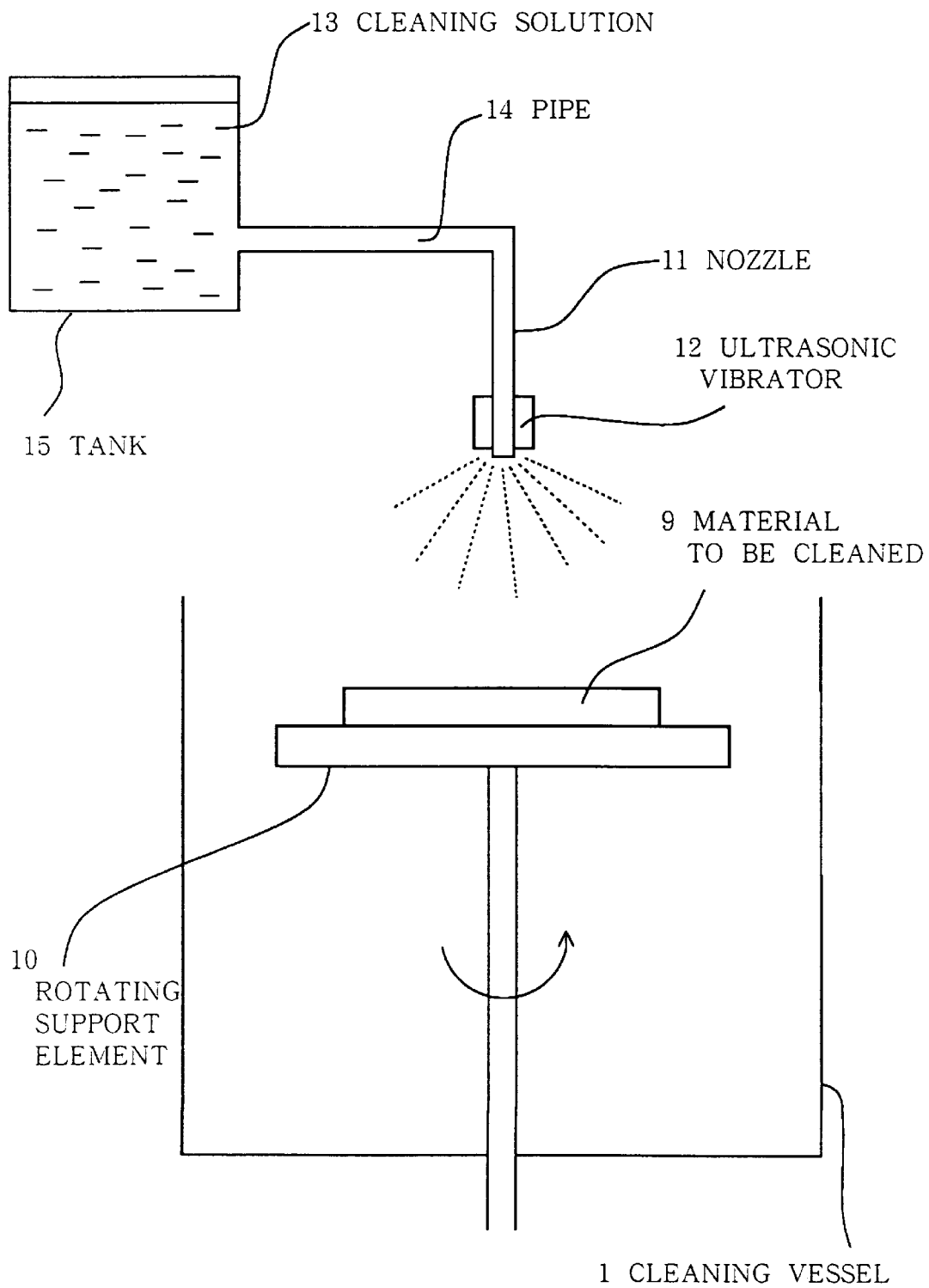
FIG. 2 is a schematic diagram showing a spray type cleaning apparatus.

In the present embodiment, in place of an immersion method, cleaning was conducted by means of a spray using the apparatus shown in FIG. 2. The material to be cleaned was rotated. This embodiment was identical to embodiment 1 in all other respects.

In the present embodiment, the removal efficiency was higher than that seen in embodiment 1.

(Embodiment 8)

In the present embodiment, the efficiency of removal of alumina and silica was investigated. The removal efficiency which was obtained with respect to these particles was identical to that of embodiment 1.

(Embodiment 9)

In the present embodiment, the effects of a surfactant were investigated. That is to say, in the present embodiment, cleaning was conducted without using a surfactant. This embodiment was identical to embodiment 1 in all other respects.

The results are as given below.

Presence of a surfactant: 96%

Absence of a surfactant: 94%

(Effects of the Invention)

The following effects were achieved by means of the present invention.

(1) The number of processes was extremely low.

(2) Treatment was possible at room temperature.

(3) The amount of chemical and water employed was reduced.

(4) Only acidic chemicals were employed, so that recovery was simplified.

What is claimed is:

1. A cleaning solution, comprising pure water containing 20 ppb–100 ppb of oxygen and 2 ppb or more of nitrogen, said pure water having impurities present at a level of 10 ppb or less.

2. A cleaning solution in accordance with claim 1, wherein the amount of oxygen contained is within a range of 40 ppb–100 ppb.

3. A cleaning solution, comprising electrolytically ionized water containing OH', and containing 20 ppb–100 ppb of oxygen, said water having impurities present at a level of 10 ppb or less.

4. A cleaning solution in accordance with claim 3, wherein the amount of oxygen contained is within a range of 40 ppb–100 ppb.

5. A cleaning method, wherein the cleaning of a material to be cleaned is conducted in a cleaning solution comprising pure water and containing 20 ppb–100 ppb of oxygen, and 2 ppb–15 ppm of nitrogen, while applying ultrasound having a frequency of 30 kHz or more.

6. A cleaning method in accordance with claim 5, wherein the cleaning solution contains impurities at a level of 10 ppb or less.

7. A cleaning method in accordance with claim 6, wherein cleaning is conducted while spraying solution onto the material to be cleaned.

8. A cleaning method in accordance with claim 6, wherein the amount of oxygen contained in the cleaning solution is within a range of 40 ppb–100 ppb.

9. A cleaning method in accordance with claim 8, wherein cleaning is conducted while spraying cleaning solution onto the material to be cleaned.

10. A cleaning method in accordance with claim 6, which is employed in cleaning wherein the material to be cleaned comprises semiconductor substrates, liquid crystal substrates, magnetic substrates, or superconducting substrates.

11. A cleaning method in accordance with claim 10, wherein cleaning is conducted while spraying cleaning solution onto the material to be cleaned.

12. A cleaning method in accordance with claim 6, wherein the material to be cleaned comprises medical supplies.

13. A cleaning method in accordance with claim 12, wherein cleaning is conducted while spraying cleaning solution onto the material to be cleaned.

14. A cleaning method in accordance with claim 6, wherein the material to be cleaned comprises foodstuffs.

15. A cleaning method in accordance with claim 6, wherein cleaning is conducted while rotating the material to be cleaned.

16. A cleaning method in accordance with claim 15, wherein cleaning is conducted while spraying cleaning solution onto the material to be cleaned.

17. A cleaning method in accordance with claim 5, wherein the amount if oxygen contained in the cleaning solution is within a range of 40 ppb–100 ppb.

18. A cleaning method in accordance with claim 17, wherein cleaning is conducted while spraying cleaning solution onto the material to be cleaned.

19. A cleaning method in accordance with claim 5, which is employed in cleaning wherein the material to be cleaned comprises a semiconductor substrate.

20. A cleaning method in accordance with claim 19, wherein cleaning is conducted while spraying cleaning solution onto the material to be cleaned.

21. A cleaning method in accordance with claim 5, wherein the material to be cleaned comprises medical supplies.

22. A cleaning method in accordance with claim 21, wherein cleaning is conducted while rotating the material to be cleaned.

23. A cleaning method in accordance with claim 22, wherein cleaning is conducted while spraying cleaning solution onto the material to be cleaned.

24. A cleaning method in accordance with claim 21, wherein cleaning is conducted while spraying cleaning solution onto the material to be cleaned.

25. A cleaning in accordance with claim 5, wherein the material to be cleaned comprises foodstuffs.

26. A cleaning method in accordance with claim 25, wherein cleaning is conducted while spraying cleaning solution onto the material to be cleaned.

27. A cleaning method in accordance with claim 5, wherein cleaning is conducted while rotating the material to be cleaned.

28. A cleaning method in accordance with claim 27, wherein cleaning is conducted while spraying cleaning solution onto the material to be cleaned.

29. A cleaning method in accordance with claim 5, wherein cleaning is conducted while spraying cleaning solution onto the material to be cleaned.

30. A cleaning method in accordance with claim 29, wherein the cleaning solution is sprayed in the form of a mist.

31. A cleaning method in accordance with claim 5, wherein cleaning is conducted by immersing the material to be cleaned in the cleaning solution.

32. A cleaning method in accordance with claim 31, wherein an inert gas gas-curtain is formed above the cleaning solution, and cleaning is conducted while isolating the cleaning solution from the atmosphere.

33. A cleaning method in accordance with claim 5, wherein the material to be cleaned comprises a liquid crystal substrate.

34. A cleaning method in accordance with claim 5, wherein the material to be cleaned comprises a magnetic substrate.

35. A cleaning method in accordance with claim 5, wherein the material to be cleaned comprises a superconducting substrate.

36. A cleaning method, wherein cleaning of a material to be cleaned is conducted in a cleaning solution comprising electrolytically ionized water containing $OH^-$ and containing 20 ppb–100 ppb of oxygen, while applying ultrasound having a frequency of 30 kHz or more.

37. A cleaning method in accordance with claim 36, wherein the cleaning solution contains impurities in an amount of 10 ppb or less.

38. A cleaning method in accordance with claim 36, wherein the amount of oxygen contained in the cleaning solution is within a range of 40 ppb–100 ppb.

39. A cleaning method in accordance with claim 36, which is used for cleaning wherein the material to be cleaned comprises a semiconductor substrate.

40. A cleaning method in accordance with claim 36, wherein the material to be cleaned comprises medical supplies.

41. A cleaning method in accordance with claim 36, wherein the material to be cleaned comprises foodstuffs.

42. A cleaning method in accordance with claim 36, wherein cleaning is conducted while rotating the material to be cleaned.

43. A cleaning method in accordance with claim 36, wherein cleaning is conducted while spraying the cleaning solution onto the material to be cleaned.

44. A cleaning method in accordance with claim 43, wherein the cleaning solution is sprayed in the form of a mist.

45. A cleaning method in accordance with claim 44, wherein an inert gas gas-curtain is formed above the cleaning solution, and cleaning is conducted while isolating the cleaning solution from the atmosphere.

46. A cleaning method in accordance with claim 36, wherein cleaning is conducted by immersing the material to be cleaned in the cleaning solution.

47. A cleaning method, wherein the cleaning of a material to be cleaned is conducted in a cleaning solution comprising pure water, containing 20 ppb–100 ppb of oxygen and 2 ppb or more nitrogen.

48. A cleaning method in accordance with claim 47, wherein the cleaning solution contains impurities at a level of 10 ppb or less.

49. A cleaning method in accordance with claim 47, wherein the amount of oxygen contained in the cleaning solution is within a range of 40 ppb–100 ppb.

50. A cleaning method in accordance with claim 47, wherein the material to be cleaned is a semiconductor substrate.

51. A cleaning method in accordance with claim 47, wherein the material to be cleaned is a liquid crystal substrate.

52. A cleaning method in accordance with claim 47, wherein the material to be cleaned is a magnetic substrate.

53. A cleaning method in accordance with claim 47, wherein the material to be cleaned is a superconducting substrate.

* * * * *

UNITED STATES PATENT AND TRADEMARK OFFICE
CERTIFICATE OF CORRECTION

PATENT NO. : 5,985,811
DATED : November 16, 1999
INVENTOR(S) : Toda Masayuki, et. al.

It is certified that error appears in the above-identified patent and that said Letters Patent is hereby corrected as shown below:

On the cover page:
At [75], "Toda Masayuki" should read --Masayuki Toda-- and "Juchu" should read --Juchu-shi--.

Signed and Sealed this

Twenty-fourth Day of October, 2000

Attest:

Q. TODD DICKINSON

*Attesting Officer*     *Director of Patents and Trademarks*